(12) United States Patent
Wang

(10) Patent No.: US 10,303,053 B2
(45) Date of Patent: May 28, 2019

(54) DIAZO-RESIN, PHOTORESIST COMPOSITION AND METHOD OF PREPARING SAME

(71) Applicant: BOE TECHNOLOGY GROUP CO., LTD., Beijing (CN)

(72) Inventor: Jianguo Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 14/905,453

(22) PCT Filed: Jun. 16, 2015

(86) PCT No.: PCT/CN2015/081526
§ 371 (c)(1),
(2) Date: Jan. 15, 2016

(87) PCT Pub. No.: WO2016/110051
PCT Pub. Date: Jul. 14, 2016

(65) Prior Publication Data
US 2016/0334704 A1    Nov. 17, 2016

(30) Foreign Application Priority Data

Jan. 9, 2015  (CN) .......................... 2015 1 0012836

(51) Int. Cl.
| | | |
|---|---|---|
| G03F 7/021 | (2006.01) | |
| G03F 7/30 | (2006.01) | |
| C07C 245/20 | (2006.01) | |
| C08G 16/04 | (2006.01) | |
| G03F 7/004 | (2006.01) | |

(52) U.S. Cl.
CPC ............ *G03F 7/021* (2013.01); *C07C 245/20* (2013.01); *C08G 16/04* (2013.01); *G03F 7/004* (2013.01); *G03F 7/30* (2013.01)

(58) Field of Classification Search
CPC .......... G03F 7/021; G03F 7/30; C07C 245/20
USPC .......................... 430/175, 176, 325; 534/558
See application file for complete search history.

(56) References Cited

U.S. PATENT DOCUMENTS

| | | | | |
|---|---|---|---|---|
| 6,960,419 B2 * | 11/2005 | West | ........................ | G03F 7/091 430/157 |
| 7,374,863 B2 * | 5/2008 | Sugasaki | ............... | B41C 1/1008 430/284.1 |

FOREIGN PATENT DOCUMENTS

| CN | 1065143 A | 10/1992 |
|---|---|---|
| CN | 102081306 A | 6/2011 |
| CN | 102096323 A | 6/2011 |
| CN | 102173181 A | 9/2011 |
| CN | 104262193 A | 1/2015 |
| CN | 104530342 A | 4/2015 |

OTHER PUBLICATIONS

Renxian Wang, Jinyu Chen, Weixiao Cao, Synthesis and Characterization of N-emthyl-2-nitro-diphenylamine-4-diazonium Salt and Its Diazoresin, Jan. 31, 1999, Journal of Applied Polymer Science, vol. 74, 189-193.*
Extended Search Report dated Jun. 13, 2017 issued in corresponding European Application No. 15832938.3.
Fourth Office Action dated Apr. 12, 2017 issued in corresponding Chinese Application No. 201510012836.8.
Wang, et al., "Synthesis and Characterization of N-Methyl-2-nitro-diphenylamine-4-diazonium Salt and Its Diazoresin", Journal of Applied Polymer Sci, vol. 74, pp. 189-193, 1999.
Form PCT/ISA/210 issued in corresponding international application No. PCT/CN2015/081526 dated Sep. 30, 2015.
Form PCT/ISA/220 issued in corresponding international application No. PCT/CN2015/081526 dated Sep. 30, 2015.
Form PCT/ISA/237 issued in corresponding international application No. PCT/CN2015/081526 dated Sep. 30, 2015.
Wang, et al., "Synthesis and Characterization of N-Methyl-2-nitrodiphenylamine-4-diazonium Salt and Its Diazoresin", Journal of Applied Polymer Science, vol. 74, 189-193, (1999).
1st office action issued in corresponding Chinese application No. 201510012836.8 dated Feb. 22, 2016. Jinyu Chen, "Photochemical and Thermal Decomposition of Diphenylamine Diazonium Salt, Resin-based Complex, and Self-assembly Study", Nov. 15, 2006, 132 pages, ISSN 1671-6779 CN 11-9246/G, Chinese Academic Journal (CD) E-magazine Press, Beijing, China.
2nd office action issued in corresponding Chinese application No. 201510012836.8 dated Apr. 27, 2016.

* cited by examiner

*Primary Examiner* — John S Chu
(74) *Attorney, Agent, or Firm* — Nath, Goldberg & Meyer; Joshua B. Goldberg

(57) ABSTRACT

Diazo-resin-containing photoresist compositions and methods of preparing the same are provided for solving the problem that existing diazo-resins cannot be applied in LCD photoresists because the storage periods of the diazo-resins themselves and the printed boards made thereby are both short due to poor thermal stability of the diazo-resins. The diazo-resins of the present invention have excellent thermal stability and exhibit strong resistance to dry etching when being used in negative photoresists, while high resolution can be achieved. Meanwhile, during exposure, portions of the diazo-resins can crosslink with hydrogen bonds on surface of SiO or SiON film forming a barrier layer or passivation layer, such that the adhesion between the photoresists and the film layer is increased, and the photoresists would not peel during development. Thus, the utilization of tackifiers for enhancing the adhesion between a photoresist and surface of SiO or SiON film before masking can be omitted.

7 Claims, 2 Drawing Sheets

DIAZO-RESIN, PHOTORESIST COMPOSITION AND METHOD OF PREPARING SAME

This is a National Phase Application filed under 35 U.S.C. 371 as a national stage of PCT/CN2015/081526, filed Jun. 16, 2015, an application claiming the benefit of Chinese Application No. 201510012836.8, filed Jan. 9, 2015, the content of each of which is hereby incorporated by reference in its entirety.

FIELD OF THE INVENTION

This invention relates to the field of polymers, and particularly, to a diazo-resin, a photoresist composition and a method of preparing the same.

BACKGROUND OF THE INVENTION

Photoresists are functional materials crucial to the photolithography processes in large-scale integrated circuit industry. When a photoresist is exposed to ultraviolet radiation, it undergoes a series of chemical reactions, such that after the exposure the dissolution rate thereof in a developing solution is different from that before the exposure. Then, by the processes of developing, film hardening, etching, film removing and so on, specific high precision graphics can be transferred onto the surface of a substrate to be processed.

However, existing diazo-resins cannot be applied in photoresists because the storage periods of the diazo-resins per se and the printed boards made thereby are both short due to the poor thermal stability of the diazo-resins.

SUMMARY OF THE INVENTION

In order to solve the above problem, the present invention provides a diazo-resin with excellent thermal stability, as described hereinafter.

The diazo-resin is represented by the following structural formula:

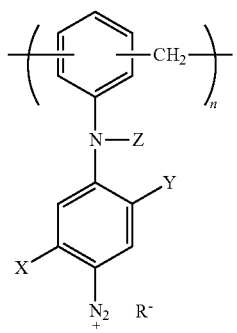

wherein, n represents an integer of 2 to 1000;

$R^-$ represents an anion selected from hexafluorophosphate, dodecylbenzene sulfonate, dodecyl sulfonate, p-toluenesulfonate, mesitylene sulfonate, and naphthalene sulfonate anions;

X represents any one selected from hydrogen, a methoxy group, and a methyl group:

Y represents a nitro group; and

Z represents a methyl group or an ethyl group.

For example, n may be 2, 5, 10, 25, 50, 75, 100, 200, 300, 400, 500, 600, 700, 800, 900 or 1000. Preferably, n is an integer of 2 to 10.

It is preferable that n is 6; $R^-$ is a mesitylene sulfonate anion; X is hydrogen; and Z is a methyl group.

Another object of the present invention is to provide a photoresist composition, comprising: 4 to 6 parts by mass of film-forming resin; 10 to 15 parts by mass of diazo-resin; 0.1 to 1 part by mass of background dye; and 200 to 300 parts by mass of organic solvent.

Preferably, the film-forming resin includes one or more selected from epoxy resins, polyvinyl acetal resins, and polyurethane resins.

Preferably, the background dye includes one or more selected from basic brilliant blue, crystal violet, Victoria pure blue, indigo blue, methyl violet, malachite green, and oil soluble blue.

Preferably, the organic solvent includes one or more selected from ethylene glycol monomethyl ether, ethylene glycol monoethyl ether, propylene glycol monoethyl ether, methyl ethyl ketone, butyl acetate, dioxane, N-methylpyrrolidone, methanol, and tetrahydrofuran.

Yet another object of the present invention is to provide a method of preparing the photoresist composition, comprising the following steps:

dissolving the background dye into the organic solvent to form a solution, followed by adding and dissolving the film-forming resin and the diazo-resin into the solution; and filtering the resultant mixture to obtain the photoresist composition.

The diazo-resins, the photoresist compositions and the preparation methods according to the present invention can produce advantageous effects. The diazo-resins have excellent thermal stability and exhibit strong resistance to dry etching when being used in negative photoresists, while high resolution can be achieved. Meanwhile, during the exposure process, portions of the diazo-resins can crosslink with hydrogen bonds on the surface of SiO or SiON film forming a barrier layer or passivation layer, such that the adhesion between the photoresists and the film layer is increased, and the photoresists would not peel during the development process. Thus, the utilization of tackifiers for enhancing the adhesion between a photoresist and the surface of SiO or SiON film before masking can be omitted.

DETAILED DESCRIPTION OF CERTAIN EMBODIMENTS

To enable a person skilled in the art to better understand the technical solution of the present invention, the invention will be further described in detail with reference to the drawings and specific embodiments.

The raw materials and equipments used in the experiments are described as follows:

N-ethylaniline and N-methylaniline are obtained from Alfa Aesar Company; sulfuric acid, 20% fuming sulfuric acid, acetic anhydride, sodium carbonate, 36% hydrochloric acid, ethanol, sodium nitrite, paraformaldehyde, $Na_2SiO_3$, and Na$_2$S are obtained from Beijing Chemical Reagent Company; 98% nitric acid, sodium azide, 1,2-dichloroethane, zinc chloride, dimethyl formamide, benzyl alcohol, sodium dodecyl sulfate, sodium mesitylene sulfonate, sodium hexafluorophosphate, and sodium naphthalene sulfonate are obtained from Beijing Coupling Technology Company; 2,4-dinitrochlorobenzene, 2,4-dinitro-5-methoxy-chlorobenzene, 5-methyl-2,4-dinitro-chlorobenzene. DDS diazo-resin in Comparative Example 1, and 2,3,4-trihydroxy benzophenone and 2-diazo-1-naphthoquinone-5-sulfonyl chloride in Comparative Example 2 are obtained from Taixing Oriental Industrial Company. All the commercially available reagents have purity of reagent grade, and they are used directly unless otherwise specified.

$^1$H NMR and $^{13}$C NMR are measured by Bruker Avame PRX400 NMR Spectrometer, chemical shifts are expressed in ppm, and the solvent depends on the solubility of the product to be measured; Infrared spectra are measured by Nicolet Avatar 360 FT-IR infrared spectrometer, liquid samples are measured by the liquid film method, and solid samples are measured by the KBr Pellets method; UV absorption spectra are measured by Cintra10e UV-Vis spectrometer (GBC Company, Australia); Elemental analysis is measured by VarioEL Elemental analyzer, MS is measured by Quattro microtriple quadrupole Mass Spectrometer (Micromass, Manchester. UK); Thermal gravimetric analysis (TGA) is measured by ZRY-2P Thermal Analyzer; Column of GPC (YL9100, Young In Scientific Co., Ltd., Korea Republic) is WAT011535 Ultrahydrogel 1000 (Waters Corp., USA), and polyvinyl alcohol is used as a standard. The type of platemaker is SBK-III (Qufu Normal University).

Example 1

This Example provides a diazo-resin having the following structural formula:

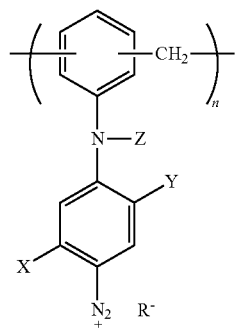

wherein, n is 6; R$^-$ is a mesitylene sulfonate anion; X is hydrogen; Y is a nitro group; and Z is an ethyl group.

This Example also provides a method of preparing the above diazo-resin, comprising the following steps:

1. Synthesis of N-ethyl-2-nitro-diphenylamine-4-diazonium salt

Figure 1:
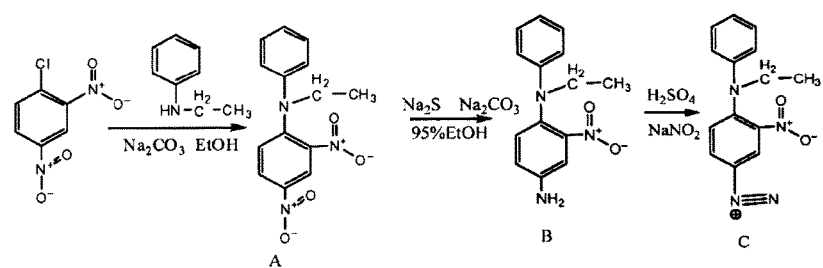
FIG. 1 is a flow chart for preparing a diazonium salt monomer of the diazo-resin in Example 1 according to the present invention.

Specific synthetic route is shown in FIG. 1. And specific synthesis steps are as follows:

1.1) Reaction of 2,4-dinitrochlorobenzene with N-ethylaniline 1.49 mol 2,4-dinitrochlorobenzene was added into 1485 ml absolute ethanol and heated to dissolve, and then 1.63 mol anhydrous Na$_2$CO$_3$ was added to form a mixture. The mixture was heated to reflux, and 1.63 mol N-ethylaniline was added dropwise over 0.5 hour. After completion of the addition, the resultant mixture was allowed to further react for 6 hours, then cooled and left aside for 12 hours, thereby a large amount of dark red prismatic monocrystalline A was obtained.

1.2) Reduction Reaction of the Product a with Na$_2$S to Generate N-ethyl-2-nitro-diphenylamine B 0.63 mol of the product A was dissolved in 1000 ml of 95% ethanol (unless specified otherwise, "%" represents "wt %" in the Specification), and then 0.63 mol anhydrous Na$_2$CO$_3$ was added to form a mixture. The mixture was heated to reflux, and a solution of 1.25 mol Na$_2$S.9H$_2$O dissolved in 500 ml water was slowly added dropwise over about 2 hours, after which the reaction mixture was refluxed for 4 hours, and then cooled. The reaction mixture was poured into 2000 ml water and allowed to stand for a period of time to stratify into layers. The upper layer (aqueous phase) was decanted, and the oil phase was washed with a bit of water, and then the resultant aqueous phase was decanted again, thereby a brown oil B, namely, N-ethyl-2-nitro-diphenylamine, was obtained. The product B should be converted into a sulfate salt because the amine group on the benzene ring is unstable and tends to be oxidized in the atmosphere.

1000 ml of 10% H$_2$SO$_4$ solution was added to the oil B and the resultant mixture was heated to 65° C. to dissolve the oil. The resultant solution was filtered while still hot, then was cooled and crystallized. Residual oil was recrystallized several times using this saturated solution until no more crystal was precipitated. A large amount of golden flaky crystals being the sulfate of B were obtained.

1.3) Diazotization Reaction of the Sulfate of B with NaNO$_2$ 0.28 mol of the sulfate of B was added into 360 ml of 5% H$_2$SO$_4$ solution, and 600 g crushed ice was added. The temperature of the resultant mixture was maintained at 0-5° C. by an ice-water bath. An aqueous solution of 0.33 mol NaNO$_2$ dissolved in 110 ml water was slowly added dropwise to the mixture under stirring. After completion of the addition, the resultant mixture was continued stirring for 2 hours, thereby a diazonium bisulfate C was generated.

The liquid mixture obtained after the reaction was filtered. When 151 g saturated solution of ZnCl$_2$ was added into the filtrate, a large amount of yellow solid was precipitated. The solid was suction filtered, washed with ethanol twice, and air-dried in a fume cupboard, thereby ½ ZnCl$_2$ complex salt D of the diazonium bisulfate C was generated.

The ½ ZnC$_2$ complex salt D of the diazonium salt C was measured and the results were as follows:

IR data:

IR (cm$^{-1}$): v=2981.4 cm$^{-1}$ (w, H$_2$C—H), 2224.0 cm$^{-1}$ (s, C—N$_2^+$), 1601 cm$^{-1}$, 1581 cm$^{-1}$, 1537 cm$^{-1}$ (vs, Ar);

NMR data:

$^1$H NMR (400 MHz, D$_2$O, δ): 8.67 (d, 1H, H Ar—NO$_2$), 8.19 (t, 1H, H Ar—N$_2$), 7.54, 7.30, 7.23, 7.14 (m, 6H, H Ar), 4.05 (q, 2H, CH$_2$), 1.12 (t, 3H, CH$_3$)

C$_{14}$H$_{13}$N$_4$O$_2^+$.HSO$_4^-$ was subjected to elemental analysis, and the results were reported in Table 1.

TABLE 1

| Data obtained by elemental analysis of $C_{14}H_{13}N_4O_2{}^+ \cdot HSO_4{}^-$ | | | |
|---|---|---|---|
| | Element C (%) | Element H (%) | Element N (%) |
| Theoretical value | 45.90 | 3.85 | 15.39 |
| Measured value | 44.42 | 3.46 | 14.73 |

Table 1 shows that the measured mass percentages of the respective elements are extremely close to the theoretical values thereof, so the formula above is correct.

2. Preparation of Water-Soluble Paraformaldehyde Condensed Diazo-Resin E

The above diazonium salt D was condensed with paraformaldehyde to prepare a diazo-resin. The polymerization process is as follows:

Diazonium salt D (0.039 mol) was added batchwise to 52 ml of 98% sulfuric acid under stirring. After the diazonium salt D was dissolved completely, 0.047 mol finely-pulverized paraformaldehyde was added batchwise at a temperature of 0-5° C. After completion of the addition, the temperature was maintained for 5 hours. The reaction mixture was slowly poured into 230 ml frozen ethanol and stirred to form a precipitate. The solid obtained by filtration was dissolved in sufficient water, and then a sufficient amount of saturated solution of $ZnCl_2$ was added to precipitate a large amount of solid. The solid was suction filtered, washed with ethanol twice, and air-dried in a fume cupboard, thereby the corresponding water-soluble paraformaldehyde condensed diazo-resin E was obtained.

3. Preparation of Paraformaldehyde Condensed N-ethyl-2-nitro-diphenylamine-4-diazo mesitylene sulfonate resin The above water-soluble paraformaldehyde condensed diazo-resin E (0.04 mol) was dissolved in 200 ml water and filtered to remove impurities. A saturated aqueous solution containing 0.045 mol sodium mesitylene sulfonate was added dropwise into the filtrate under stirring, and anion exchange occurred from pH 2.5. 10% $Na_2CO_3$ solution was added to adjust pH to 7. The resulting precipitate was suction filtered, washed with water three times, and dried at 27° C. under vacuum overnight, thereby the paraformaldehyde condensed N-ethyl-2-nitro-diphenylamine-4-diazo mesitylene sulfonate resin was obtained (yield: 77%).

The paraformaldehyde condensed N-ethyl-2-nitro-diphenylamine-4-diazo mesitylene sulfonate resin was measured and the resulting data are as follows:

IR data:

IR ($cm^{-1}$): v=2971.8 $cm^{-1}$ (w, $H_2C$—H), 2200.0 $cm^{-1}$ (s, C—$N_2$), 1588.2 $cm^{-1}$, 1543.4 $cm^{-1}$ (vs, Ar);

NMR data:

$^1H$ NMR (400 MHz, $D_2O$, δ): 8.67 (d, 1H, H—Ar—$NO_2$), 8.19 (t, 1H, H—Ar—$N_2{}^+$), 7.54, 7.30, 7.23, 7.14 (m, 6H, H—Ar), 4.05 (q, 2H, $CH_2$), 1.12 (t, 3H, $CH_3$).

Figure 2:
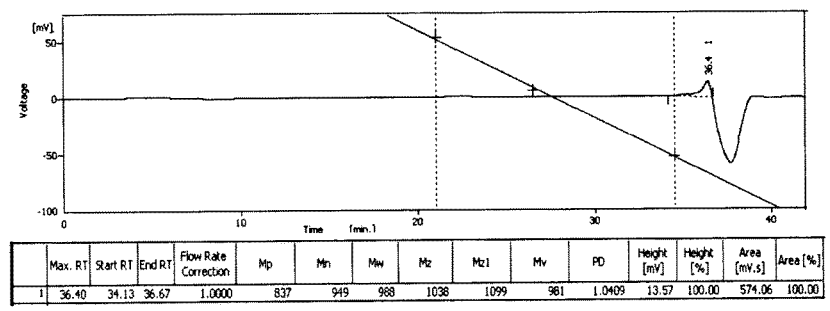
FIG. 2 is a diagram showing the result of the molecular weight distribution measurement of the diazo-resin in Example 1 according to the present invention.

Molecular Weight Distribution:

The molecular weight distribution of the resin was measured by GPC, and the chromatogram as measured and the results calculated by inbuilt software of the system were shown in FIG. 2.

Example 2

This Example provides a diazo-resin having the following structural formula:

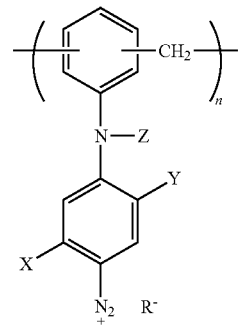

wherein, n is 2; R is a dodecyl sulfonate anion; X is a methoxy group; Y is a nitro group; and Z is a methyl group.

This Example also provides a method of preparing the above diazo-resin, comprising the following steps:

1. Synthesis of N-methyl-2-nitro-5-methoxy-diphenylamine-4-diazonium salt

Specific synthetic route is similar to that shown in FIG. 1. And specific synthesis steps are as follows:

1.1) Reaction of 2,4-dinitro-5-methoxy-chlorobenzene with N-methylaniline 1.49 mol 2,4-dinitro-5-methoxy-chlorobenzene was added into 1485 ml absolute ethanol and heated to dissolve, and then 1.63 mol anhydrous $Na_2CO_3$ was added to form a mixture. The mixture was heated to reflux, and 1.63 mol N-methylaniline was added dropwise over 0.5 hour. After completion of the addition, the resultant mixture was allowed to further react for 6 hours, then cooled and left aside for 12 hours, thereby a large amount of dark red prismatic monocrystalline A1 was obtained.

1.2) Reduction Reaction of the Product A1 with $Na_2S$ to Generate N-methyl-2-nitro-5-methoxy-diphenylamine B1

0.63 mol of the product A1 was dissolved in 1000 ml of 95% ethanol, and then 0.63 mol anhydrous $Na_2CO_3$ was added to form a mixture. The mixture was heated to reflux, and a solution of 1.25 mol $Na_2S.9H_2O$ dissolved in 500 ml water was slowly added dropwise over about 2 hours, after which the reaction mixture was refluxed for 4 hours, and then cooled. The reaction mixture was poured into 2000 ml water and allowed to stand for a period of time to stratify into layers. The upper layer (aqueous phase) was decanted, and the oil phase was washed with a bit of water, and then the resultant aqueous phase was decanted again, thereby a brown oil B1, namely, N-methyl-2-nitro-5-methoxy-diphenylamine, was obtained. The product B1 should be converted into a sulfate salt because the amine group on the benzene ring is unstable and tends to be oxidized in the atmosphere.

1000 ml of 10% $H_2SO_4$ solution was added to the oil B1 and the resultant mixture was heated to 65° C. to dissolve the oil. The resultant solution was filtered while still hot, then was cooled and crystallized. Residual oil was recrystallized several times using this saturated solution until no more crystal was precipitated. A large amount of golden flaky crystals being the sulfate of B1 were obtained.

1.3) Diazotization Reaction of the Sulfate of B1 with $NaNO_2$ 0.28 mol of the sulfate of B1 was added into 360 ml of 5% $H_2SO_4$ solution, and 600 g crushed ice was added. The temperature of the resultant mixture was maintained at 0-5° C. by an ice-water bath. An aqueous solution of 0.33 mol $NaNO_2$ dissolved in 110 ml water was slowly added dropwise to the mixture under stirring. After completion of the addition, the resultant mixture was continued stirring for 2 hours, thereby a diazonium bisulfate C1 was generated.

The liquid mixture obtained after the reaction was filtered. When 151 g saturated solution of $ZnCl_2$ was added into the filtrate, a large amount of yellow solid was precipitated. The solid was suction filtered, washed with ethanol twice, and air-dried in a fume cupboard, thereby ½ $ZnCl_2$ complex salt D1 of the diazonium bisulfate C1 was generated.

2. Preparation of Water-Soluble Paraformaldehyde Condensed Diazo-Resin E1

The above diazonium salt D1 was condensed with paraformaldehyde to prepare a diazo-resin. The polymerization process is as follows:

Diazonium salt D1 (0.039 mol) was added batchwise to 52 ml of 98% sulfuric acid under stirring. After the diazonium salt D1 was dissolved completely, 0.047 mol finely-pulverized paraformaldehyde was added batchwise at a temperature of 0-5° C. After completion of the addition, the temperature was maintained for 5 hours. The reaction mixture was slowly poured into 230 ml frozen ethanol and stirred to form a precipitate. The solid obtained by filtration was dissolved in sufficient water, and then a sufficient amount of saturated solution of $ZnCl_2$ was added to precipitate a large amount of solid. The solid was suction filtered, washed with ethanol twice, and air-dried in a fume cupboard, thereby the corresponding water-soluble paraformaldehyde condensed diazo-resin E1 was obtained.

3. Preparation of Paraformaldehyde Condensed N-methyl-2-nitro-5-methoxy-diphenylamine-4-diazo dodecyl sulfonate resin The above water-soluble paraformaldehyde condensed diazo-resin E1 (0.04 mol) was dissolved in 200 ml water and filtered to remove impurities. A saturated aqueous solution containing 0.045 mol sodium dodecyl sulfate was added dropwise into the filtrate under stirring, and anion exchange occurred from pH 2.5. 10% $Na_2CO_3$ solution was added to adjust pH to 7. The resulting precipitate was suction filtered, washed with water three times, and dried at 27° C. under vacuum overnight, thereby the paraformaldehyde condensed N-methyl-2-nitro-5-methoxy-diphenylamine-4-diazo dodecyl sulfonate resin was obtained.

Example 3

This Example provides a diazo-resin having the following structural formula:

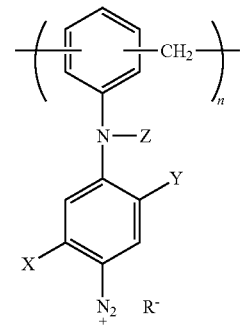

wherein, n is 1000; $R^-$ is a hexafluorophosphate anion; X is a methyl group; Y is a nitro group; and Z is an ethyl group.

This Example also provides a method of preparing the above diazo-resin, comprising the following steps:

1. Synthesis of N-ethyl-5-methyl-2-nitro-diphenylamine-4-diazonium salt

Specific synthetic route is similar to that shown in FIG. 1. And specific synthesis steps are as follows:

1.1) Reaction of 5-methyl-2,4-dinitro-chlorobenzene with N-ethylaniline 1.49 mol 5-methyl-2,4-dinitro-chlorobenzene was added into 1485 ml absolute ethanol and heated to dissolve, and then 1.63 mol anhydrous $Na_2CO_3$ was added to form a mixture. The mixture was heated to reflux, and 1.63 mol N-ethylaniline was added dropwise over 0.5 hour. After completion of the addition, the resultant mixture was allowed to further react for 6 hours, then cooled and left aside for 12 hours, thereby a large amount of dark red prismatic monocrystalline A2 was obtained.

1.2) Reduction Reaction of the Product A2 with $Na_2S$ to Generate N-ethyl-5-methyl-2-nitro-diphenylamine B2

0.63 mol of the product A2 was dissolved in 1000 ml of 95% ethanol, and then 0.63 mol anhydrous $Na_2CO_3$ was added to form a mixture. The mixture was heated to reflux, and a solution of 1.25 mol $Na_2S.9H_2O$ dissolved in 500 ml water was slowly added dropwise over about 2 hours, after which the reaction mixture was refluxed for 4 hours, and then cooled. The reaction mixture was poured into 2000 ml water and allowed to stand for a period of time to stratify into layers. The upper layer (aqueous phase) was decanted, and the oil phase was washed with a bit of water, and then the resultant aqueous phase was decanted again, thereby a brown oil B2, namely, N-ethyl-5-methyl-2-nitro-diphenylamine, was obtained. The product B2 should be converted into a sulfate salt because the amine group on the benzene ring is unstable and tends to be oxidized in the atmosphere.

1000 ml of 10% $H_2SO_4$ solution was added to the oil B2 and the resultant mixture was heated to 65° C. to dissolve the oil. The resultant solution was filtered while still hot, then was cooled and crystallized. Residual oil was recrystallized several times using this saturated solution until no more crystal was precipitated. A large amount of golden flaky crystals being the sulfate of B2 were obtained.

1.3) Diazotization Reaction of the Sulfate of B2 with NaNO$_2$ 0.28 mol of the sulfate of B2 was added into 360 ml of 5% H$_2$SO$_4$ solution, and 600 g crushed ice was added. The temperature of the resultant mixture was maintained at 0-5° C. by an ice-water bath. An aqueous solution of 0.33 mol NaNO$_2$ dissolved in 110 ml water was slowly added dropwise to the mixture under stirring. After completion of the addition, the resultant mixture was continued stirring for 2 hours, thereby a diazonium bisulfate C2 was generated.

The liquid mixture obtained after the reaction was filtered. When 151 g saturated solution of ZnCl$_2$ was added into the filtrate, a large amount of yellow solid was precipitated. The solid was suction filtered, washed with ethanol twice, and air-dried in a fume cupboard, thereby ½ ZnCl$_2$ complex salt D2 of the diazonium bisulfate C2 was generated.

2. Preparation of Water-Soluble Paraformaldehyde Condensed Diazo-Resin E2

The above diazonium salt D2 was condensed with paraformaldehyde to prepare a diazo-resin. The polymerization process is as follows:

Diazonium salt D2 (0.039 mol) was added batchwise to 52 ml of 98% sulfuric acid under stirring. After the diazonium salt D2 was dissolved completely, 0.047 mol finely-pulverized paraformaldehyde was added batchwise at a temperature of 0-5° C. After completion of the addition, the temperature was maintained for 5 hours. The reaction mixture was slowly poured into 230 ml frozen ethanol and stirred to form a precipitate. The solid obtained by filtration was dissolved in sufficient water, and then a sufficient amount of saturated solution of ZnCl$_2$ was added to precipitate a large amount of solid. The solid was suction filtered, washed with ethanol twice, and air-dried in a fume cupboard, thereby the corresponding water-soluble paraformaldehyde condensed diazo-resin E2 was obtained.

3. Preparation of Paraformaldehyde Condensed N-ethyl-5-methyl-2-nitro-diphenylamine-4-diazo hexafluorophosphate resin The above water-soluble paraformaldehyde condensed diazo-resin E2 (0.04 mol) was dissolved in 200 ml water and filtered to remove impurities. A saturated aqueous solution containing 0.045 mol sodium hexafluorophosphate was added dropwise into the filtrate under stirring, and anion exchange occurred from pH 2.5. 10% Na$_2$CO$_3$ solution was added to adjust pH to 7. The resulting precipitate was suction filtered, washed with water three times, and dried at 27° C. under vacuum overnight, thereby the paraformaldehyde condensed N-ethyl-5-methyl-2-nitro-diphenylamine-4-diazo hexafluorophosphate resin was obtained.

Example 4

This Example provides a diazo-resin having the following structural formula:

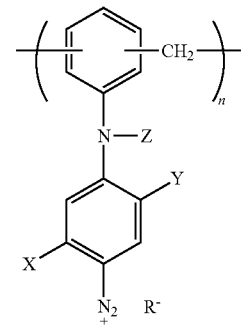

wherein, n is 10; R$^-$ is a naphthalene sulfonate anion; X is a methyl group; Y is a nitro group; and Z is a methyl group.

This Example also provides a method of preparing the above diazo-resin, comprising the following steps:

1. Synthesis of N-methyl-5-methyl-2-nitro-diphenylamine-4-diazonium salt

Specific synthetic route is similar to that shown in FIG. 1. And specific synthesis steps are as follows:

1.1) Reaction of 5-methyl-2,4-dinitro-chlorobenzene with N-methylaniline 1.49 mol 5-methyl-2,4-dinitro-chlorobenzene was added into 1485 ml absolute ethanol and heated to dissolve, and then 1.63 mol anhydrous Na$_2$CO$_3$ was added to form a mixture. The mixture was heated to reflux, and 1.63 mol N-methylaniline was added dropwise over 0.5 hour. After completion of the addition, the resultant mixture was allowed to further react for 6 hours, then cooled and left aside for 12 hours, thereby a large amount of dark red prismatic monocrystalline A3 was obtained.

1.2) Reduction Reaction of the Product A3 with Na$_2$S to Generate N-methyl-5-methyl-2-nitro-diphenylamine B3

0.63 mol of the product A3 was dissolved in 1000 ml of 95% ethanol, and then 0.63 mol anhydrous Na$_2$CO$_3$ was added to form a mixture. The mixture was heated to reflux, and a solution of 1.25 mol Na$_2$S.9H$_2$O dissolved in 500 ml water was slowly added dropwise over about 2 hours, after which the reaction mixture was refluxed for 4 hours, and then cooled. The reaction mixture was poured into 2000 ml water and allowed to stand for a period of time to stratify into layers. The upper layer (aqueous phase) was decanted, and the oil phase was washed with a bit of water, and then the resultant aqueous phase was decanted again, thereby a brown oil B3, namely, N-methyl-5-methyl-2-nitro-diphenylamine, was obtained. The product B3 should be converted into a sulfate salt because the amine group on the benzene ring is unstable and tends to be oxidized in the atmosphere.

1000 ml of 10% H$_2$SO$_4$ solution was added to the oil B3 and the resultant mixture was heated to 65° C. to dissolve the oil. The resultant solution was filtered while still hot, then was cooled and crystallized. Residual oil was recrystallized several times using this saturated solution until no more crystal was precipitated. A large amount of golden flaky crystals being the sulfate of B3 were obtained.

1.3) Diazotization Reaction of the Sulfate of B3 with NaNO$_2$ 0.28 mol of the sulfate of B3 was added into 360 ml of 5% H$_2$SO$_4$ solution, and 600 g crushed ice was added. The temperature of the resultant mixture was maintained at 0-5° C. by an ice-water bath. An aqueous solution of 0.33 mol NaNO$_2$ dissolved in 110 ml water was slowly added dropwise to the mixture under stirring. After completion of the addition, the resultant mixture was continued stirring for 2 hours, thereby a diazonium bisulfate C3 was generated.

The liquid mixture obtained after the reaction was filtered. When 151 g saturated solution of ZnCl$_2$ was added into the filtrate, a large amount of yellow solid was precipitated. The solid was suction filtered, washed with ethanol twice, and air-dried in a fume cupboard, thereby ½ ZnCl$_2$ complex salt D3 of the diazonium bisulfate C3 was generated.

2. Preparation of Water-Soluble Paraformaldehyde Condensed Diazo-Resin E3

The above diazonium salt D3 was condensed with paraformaldehyde to prepare a diazo-resin. The polymerization process is as follows:

Diazonium salt D3 (0.039 mol) was added batchwise to 52 ml of 98% sulfuric acid under stirring. After the diazonium salt D3 was dissolved completely, 0.047 mol finely-pulverized paraformaldehyde was added batchwise at a temperature of 0-5° C. After completion of the addition, the temperature was maintained for 5 hours. The reaction mixture was slowly poured into 230 ml frozen ethanol and stirred to form a precipitate. The solid obtained by filtration was dissolved in sufficient water, and then a sufficient amount of saturated solution of ZnCl$_2$ was added to precipitate a large amount of solid. The solid was suction filtered, washed with ethanol twice, and air-dried in a fume cupboard, thereby the corresponding water-soluble paraformaldehyde condensed diazo-resin E3 was obtained.

3. Preparation of Paraformaldehyde Condensed N-methyl-5-methyl-2-nitro-diphenylamine-4-diazo naphthalene sulfonate resin The above water-soluble paraformaldehyde condensed diazo-resin E3 (0.04 mol) was dissolved in 200 ml water and filtered to remove impurities. A saturated aqueous solution containing 0.045 mol sodium naphthalene sulfonate was added dropwise into the filtrate under stirring, and anion exchange occurred from pH 2.5. 10% Na$_2$CO$_3$ solution was added to adjust pH to 7. The resulting precipitate was suction filtered, washed with water three times, and dried at 27° C. under vacuum overnight, thereby the paraformaldehyde condensed N-methyl-5-methyl-2-nitro-diphenylamine-4-diazo naphthalene sulfonate resin was obtained.

From the preparation methods described above, it can be understood that 1-chloro-5-methyl-2,4-dinitro-benzene or 1-chloro-5-methoxy-2,4-dinitro-benzene may be subjected to the above reaction with N-ethylaniline or N-methylaniline to prepare the corresponding diazonium salt, and the diazonium salt may be subjected to the polymerization reaction with paraformaldehyde, and then various diazo-resins with different acid radicals can be obtained through ion exchange.

It should be appreciated that Examples 1-4 exemplarily demonstrate the preparation methods of some diazo-resins. In the case that the reactive sites are fixed, a person skilled in the art can prepare other diazo-resins with different substituents using corresponding raw materials through similar preparation methods, and thus the preparation thereof is omitted.

Example 5

This Example provides a photoresist composition and a method of preparing the same.

The photoresist composition comprises (parts by mass):
0.1 part Victoria pure blue as the background dye;
250 parts ethylene glycol monoethyl ether as the organic solvent;
10 parts paraformaldehyde condensed N-ethyl-5-methyl-2-nitro-diphenylamine-4-diazo hexafluorophosphate resin as the diazo-resin; and
5 parts polyvinyl formal maleate as the film-forming resin.

The method of preparing the photoresist composition is as follows:

0.1 g Victoria pure blue was dissolved in 250 g ethylene glycol monoethyl ether, and then 10 g paraformaldehyde condensed N-ethyl-5-methyl-2-nitro-diphenylamine-4-diazo hexafluorophosphate resin and 5 g polyvinyl formal maleate were added to form a mixture. After dissolved completely, the mixture was filtered with filter paper, thereby the photoresist was obtained.

Example 6

This Example provides a photoresist composition and a method of preparing the same.

The photoresist composition comprises (parts by mass):
0.5 part crystal violet as the background dye;
200 parts propylene glycol monoethyl ether as the organic solvent;
12 parts paraformaldehyde condensed N-methyl-2-nitro-5-methoxy-diphenylamine-4-diazo dodecyl sulfonate resin as the diazo-resin; and
6 parts polyvinyl formal phthalate as the film-forming resin.

The method of preparing the photoresist composition is as follows:

0.5 g crystal violet was dissolved in 200 g propylene glycol monoethyl ether, and then 12 g paraformaldehyde condensed N-methyl-2-nitro-5-methoxy-diphenylamine-4-diazo dodecyl sulfonate resin and 6 g polyvinyl formal phthalate were added to form a mixture. After dissolved completely, the mixture was filtered with filter paper, thereby the photoresist was obtained.

Example 7

This Example provides a photoresist composition and a method of preparing the same.

The photoresist composition comprises (parts by mass):
1 part basic brilliant blue as the background dye;
300 parts ethylene glycol monomethyl ether as the organic solvent;
15 parts paraformaldehyde condensed N-ethyl-2-nitro-diphenylamine-4-diazo mesitylene sulfonate resin as the diazo-resin; and
4 parts polyvinyl butyral phthalate as the film-forming resin.

The method of preparing the photoresist composition is as follows:

1 g basic brilliant blue was dissolved in 300 g ethylene glycol monomethyl ether, and then 15 g paraformaldehyde condensed N-ethyl-2-nitro-diphenylamine-4-diazo mesitylene sulfonate resin and 4 g polyvinyl butyral phthalate were added to form a mixture. After dissolved completely, the mixture was filtered with filter paper, thereby the photoresist was obtained.

Example 8

This Example provides a photoresist composition and a method of preparing the same.

The photoresist composition comprises (parts by mass):
0.8 part malachite green as the background dye:
300 parts methanol as the organic solvent;
14 parts paraformaldehyde condensed N-methyl-5-methyl-2-nitro-diphenylamine-4-diazo naphthalene sulfonate resin as the diazo-resin; and
4 parts polyvinyl butyral phthalate as the film-forming resin.

The method of preparing the photoresist composition is as follows:

0.8 g malachite green was dissolved in 300 g methanol, and then 14 g paraformaldehyde condensed N-methyl-5-methyl-2-nitro-diphenylamine-4-diazo naphthalene sulfonate resin and 4 g polyvinyl butyral phthalate were added to form a mixture. After dissolved completely, the mixture was filtered with filter paper, thereby the photoresist was obtained.

Comparative Example 1

The storage period of a diazo-resin is related to the thermal decomposition performance thereof in solid powder state, while the storage period of a printed board made from the diazo-resin is related to the thermal decomposition performance thereof in solid film state.

A conventional diazo-resin is diphenylamine-4-diazo-resin (DDS) having the following structure:

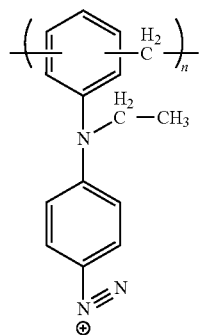

wherein n represents an integer of 2-5.

Molar thermal decomposition rate (Dt %) is obtained by calculating the reduced amount of UV absorption after heating relative to that before heating. The thermal stability of each diazo-resin is evaluated by measuring the thermal decomposition rate of the diazo-resin heated for various periods of time at a specific temperature. Herein, the thermal decomposition rate is measured at 80° C.

The conventional diazo-resin and the diazo-resins prepared by Examples 1-4 of the present invention have been subjected to thermal stability measurement. The results are reported in Table 2.

TABLE 2

Results of thermal decomposition rate measurement at 80° C. of DDS and the diazo-resins prepared according to the present invention

| | Thermal decomposition rate (mol %) | | | |
|---|---|---|---|---|
| Heating time (hour) | 9 | 18 | 24 | 34 |
| Diazo-resin prepared by Example 1 | 3 | 15 | 40 | 60 |
| Diazo-resin prepared by Example 2 | 2 | 12 | 32 | 51 |
| Diazo-resin prepared by Example 3 | 4 | 17 | 45 | 63 |
| Diazo-resin prepared by Example 4 | 5 | 20 | 50 | 65 |
| Diazo-resin of Comparative Example 1 | 100 | — | — | — |

From Table 2, it can be seen that the thermal stabilities of the nitro-containing diazo-resins prepared by Examples 1-4 of the present invention are significant better than the conventional diazo-resin. After being heated for 34 hours, the diazo-resins prepared according to the present invention have Dt % of about 60%. However, DDS resin already decomposed completely after being heated for only 9 hours. Thus, when the diazo-resins prepared according to the present invention are used as diazo sensitizers, the storage period of the diazo sensitizers would be prolonged.

Comparative Example 2

1.5 g 2,3,4-trihydroxybenzophenone esterified 2-diazo-1-naphthoquinone-5-sulfonyl chloride (the product of esterification reaction between 1 mol 2,3,4-trihydroxybenzophenone and 2.35 mol 2-diazo-1-naphthoquinone-5-sulfonyl chloride) as a sensitizer and 8.5 g linear phenolic resin were dissolved in 25 g 2-methoxyethyl acetate, and then filtered with filter paper, thereby the photoresist of Comparative Example 2 was obtained.

Meanwhile, the photoresists prepared from the diazo-resins of Examples 1-4 of the present invention were subjected to the following test as experimental group. The results are reported in Table 3.

The photoresists of Comparative Example 2 and the experimental group were coated respectively, at a rotation rate of 2000-6000 rpm, onto a glass substrate on which $SiO_2$ (thickness: 1000 Å) was already deposited by plasma enhanced chemical vapor deposition, and baked at 100° C. for 2-10 min to form films containing the respective photoresists. Then the films were exposed by an exposure device at an intensity of 30-180 $mJ/cm^2$, developed in a developing solution for 20 s, and then dried, thereby an image was obtained.

The developing solution was prepared by dissolving 1-5 parts by mass of $Na_2SiO_3$, 8-10 parts by mass of benzyl alcohol, and 4-8 parts by mass of sodium dodecyl sulfate in 80-120 parts by mass of water.

Herein, resolution refers to the minimum width that the intervening spaces between two or more equally spaced lines formed after exposure and development of the respective photoresist compositions by the above process can be reproduced on the photosurface.

Here, sensitivity refers to the minimum amount of exposure required when 3.5 μm image is formed according to the above process of exposure and development.

TABLE 3

Performance comparison between the photoresists of the present invention and the photoresist of Comparative Example 2

| Examples | Resolution (μm) | photoresist peeled or not |
|---|---|---|
| Example 1 | 3.0 | Not |
| Example 2 | 3.2 | Not |
| Example 3 | 3.1 | Not |
| Example 4 | 2.9 | Not |
| Comparative Example 2 | 3.1 | peeled off in a large area |

From Table 3, it can be seen that when the diazo-resins of the present invention are applied in negative photoresists, the photoresists exhibit strong resistance to dry etching and achieve high resolution due to crosslinking.

In addition, during the exposure process, portions of the diazo-resins can crosslink with hydrogen bonds on the surface of SiO or SiON film of the barrier layer or passivation layer, such that the adhesion between the photoresists and the film layer is increased, and the photoresist would not peel during the development process. Thus, the utilization of tackifiers for enhancing the adhesion between a photoresist and the surface of SiO or SiON film before masking can be omitted.

Figure 3:
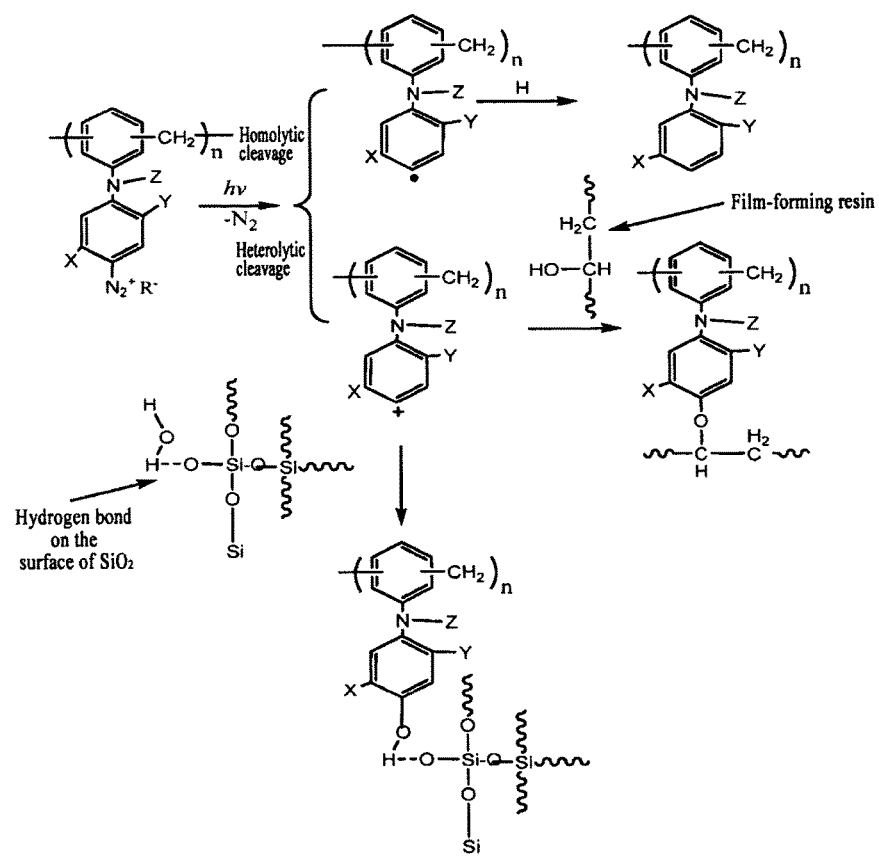
FIG. 3 is a diagram showing the principle why the diazo-resin of the present invention can achieve higher sensitivity and resolution.

Specific principle is shown in FIG. 3. During the exposure process, for the sake of the electron withdrawing effect from the nitro group, the diazo phenyl group mainly undergoes heterolytic cleavage to generate a large amount of diphenylamine cations. In addition to react with —OH nucleophile on the film-forming resin, the diphenylamine cations also crosslink with the hydrogen bonds formed between the surface of $SiO_2$ film and water molecules. As a result, the exposed portions of the photoresist bond with the surface of $SiO_2$ by hydrogen bonds, so that the photoresist would not peel during development; on the contrary, the unexposed portions of the photoresist do not form such bonding and are removed after development. Accordingly, the solubility difference between the exposed portions and the unexposed portions is significantly enhanced, while the sensitivity and resolution are also increased.

It is appreciated that the above embodiments are merely exemplary embodiments employed to illustrate the principles of the present invention, but the present invention is not limited thereto. Those of ordinary skill in the art may make various changes and improvements without departing from the spirit and essence of the present invention, and such variations and modifications are also encompassed in the scope of the present invention.

The invention claimed is:

1. A photoresist composition for photolithography processes in a large-scale integrated circuit industry, comprising: 4 to 6 parts by mass of film-forming resin; 10 to 15 parts by mass of a diazo-resin; 0.1 to 1 part by mass of background dye; and 200 to 300 parts by mass of organic solvent, wherein, in the photolithography processes, a SiO or SiNO film is used to form a barrier layer or passivation layer, and wherein the diazo-resin has the following structural formula:

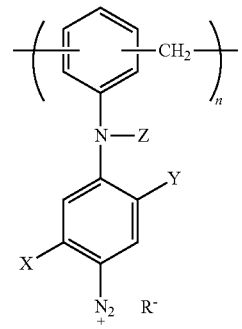

wherein n represents an integer of 10 to 1000;

$R^-$ represents an anion selected from hexafluorophosphate, dodecylbenzene sulfonate, dodecyl sulfonate, p-toluenesulfonate, mesitylene sulfonate, and naphthalene sulfonate anions;

X represents a methoxy group;

Y represents a nitro group; and

Z represents a methyl group or an ethyl group.

2. The photoresist composition according to claim 1, characterized in that, said film-forming resin includes one or more selected from epoxy resins, polyvinyl acetal resins, and polyurethane resins.

3. The photoresist composition according to claim 1, characterized in that, said background dye includes one or more selected from basicbrilliantblue, crystal violet, Victoria pure blue, indigo blue, methyl violet, malachite green, and oil soluble blue.

4. The photoresist composition according to claim 1, characterized in that, said organic solvent includes one or more selected from ethylene glycol monomethyl ether, ethylene glycol monoethyl ether, propylene glycol monoethyl ether, methyl ethyl ketone, butyl acetate, dioxane, N-methylpyrrolidone, methanol, and tetrahydrofuran.

5. A method of preparing the photoresist composition according to claim 1, comprising the following steps:

dissolving the background dye into the organic solvent to form a solution, followed by adding and dissolving the film-forming resin and the diazo-resin into the solution; and filtering the resultant mixture to obtain the photoresist composition.

6. The photoresist composition according to claim 1, characterized in that n is 1000.

7. A photoresist composition, comprising: 4 to 6 parts by mass of film-forming resin; 10 to 15 parts by mass of a diazo-resin; 0.1 to 1 part by mass of background dye; and 200 to 300 parts by mass of organic solvent, wherein, the diazo-resin has the following structural formula:

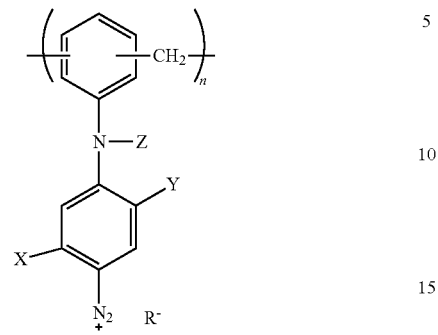

wherein n represents an integer of 10 to 1000;
R⁻ represents an anion selected from hexafluorophosphate, dodecylbenzene sulfonate, dodecyl sulfonate, p-toluenesulfonate, mesitylene sulfonate, and naphthalene sulfonate anions;
X represents a methoxy group;
Y represents a nitro group; and
Z represents a methyl group or an ethyl group.

* * * * *